United States Patent [19]

Hester, Jr.

[11] 3,991,070

[45] Nov. 9, 1976

[54] PROCESS FOR PREPARING HALO TRIAZOLO BENZODIAZEPINE

[75] Inventor: Jackson B. Hester, Jr., Galesburg, Mich.

[73] Assignee: The Upjohn Company, Kalamazoo, Mich.

[22] Filed: Sept. 26, 1976

[21] Appl. No.: 616,955

[52] U.S. Cl. .................................. 260/308 R
[51] Int. Cl.² ................................. C07D 487/04
[58] Field of Search .......................... 260/308 R

[56] References Cited
UNITED STATES PATENTS

| | | | |
|---|---|---|---|
| 3,709,899 | 1/1973 | Hester | 260/308 R |
| 3,842,090 | 10/1974 | Gall et al. | 260/308 R |
| 3,880,878 | 4/1975 | Hester | 260/308 R |
| 3,882,139 | 5/1975 | Gall et al. | 260/308 R |
| 3,891,666 | 6/1975 | Hester | 260/308 R |

*Primary Examiner*—Alton D. Rollins
*Attorney, Agent, or Firm*—John T. Reynolds

[57] ABSTRACT

Preparing 1-halo-6-phenyl-4H-s-triazolo[4,3-a][1,4]benzodiazepines by reacting an N-halosuccinimide with a 2-[3-(phthalimidomethyl)-triazolyl]benzophenone to form the 2-[5-halo-3-(phthalimidomethyl)triazolyl]benzophenone and reacting the 2-[5-halo-3-(phthalimidomethyl)triazol-4-yl]benzophenone with hydrazine or a primary amine in an organic liquid solvent medium at 25° to 100° C. The products of the process have CNS tranquilizer and sedative properties but are also of interest for use as intermediates to prepare 2,4-dihydro-6-phenyl-1H-s-triazolo[4,3-a][1,4]benzodiazepin-1-ones which are of clinical interest for their CNS tranquilizer, sedative and anti-depressant drug use properties in mammalian animals including humans.

4 Claims, No Drawings

PROCESS FOR PREPARING HALO TRIAZOLO BENZODIAZEPINE

INTRODUCTION

This invention relates to a process for preparing halo-triazolobenzodiazepines from benzophenone starting materials. More particularly, this invention provides an improved process for preparing 1-halo-6-phenyl-4H-s-triazolo[4,3-a][1,4]-benzodiazepines from 3-(phthalimidomethyl)-substituted triazolylbenzophenones, and more particularly from 2-[5-halo-3-(phthalimidomethyl)triazol-4-yl]benzophenones and hydrazine or primary amines.

BACKGROUND OF THE INVENTION

1-Halo-6-phenyl-4H-s-triazolo[4,3-a][1,4]benzodiazepines of the formula

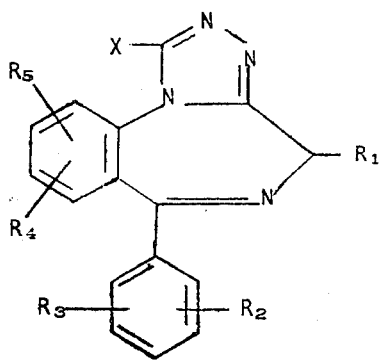

wherein X is chlorine or bromine, $R_1$ is hydrogen or $C_1$ to $C_3$-alkyl, and the $R_2$, $R_3$, $R_4$ and $R_5$ are hydrogen, $C_1$ to $C_3$-alkyl, fluoro, chloro, bromo, nitro, cyano and trifluoromethyl, are known compounds being included in the description of U.S. Pat. No. 3,709,899. These compounds have sedative, tranquilizing and muscle relaxing properties in mammals and birds and they are useful as drugs where sedation, tranquilization or muscle relaxing effects are desired. These compounds are now also of interest for their use as intermediates in the preparation of the corresponding 2,4-dihydro-6-phenyl-1H-s-triazolo[4,3-a][1,4]benzodiazepin-1-ones by procedures now described in U.S. Pat. No. 3,856,809. Those '809 patented benzodiazepine-1-one derivatives have central nervous system sedative, transquilizing and antiolytic effects in mammals including humans, and a representative example thereof has been selected for study in humans in the clinic.

The process for preparing 1-halo-6-phenyl-4H-s-triazolo-[4,3-a][1,4]benzodiazepines described in U.S. Pat. No. 3,709,899 involves halogenation of the triazolobenzodiazepine with an N-halosuccinimide. However, that process requires the prior preparation of the triazolo-benzodiazepine which involves a multiplicity of process steps which, for economy reasons, chemical process operators would prefer to avoid.

U.S. Pat. No. 3,842,090 discloses a multi-step process for preparing a 1-substituted aminomethyl-6-phenyl-4H-s-triazolo[4,3-a][1,4]benzodiazepine. Some of the steps thereof include the formation of a 2-[3-(phthalimidomethyl)-4H-1,2,4-triazol-4-yl]benzophenone, and later in the process, reacting the 2-[1-(substituted aminomethyl)-3-(phthalimidomethyl)-triazol-4-yl]benzophenone with hydrazine hydrate to give the 1-(substituted amino)methyl-6-phenyl-4H-s-triazolo[4,3-a]-[1,4]benzodiazepine. However, at no time in that process is there a free halogen bonded to the 5-position of the triazole ring of the triazolobenzophenone derivative, so that patent does not describe or suggest the problem which has been solved by this invention.

In South African Pat. No. 74/0466 there is described a process for preparing 1-unsubstituted or 1-alkyl, 1-phenyl, 1-benzyl or 1-alkoxycarbonyl-6-phenyl-4H-s-triazolo[4,3-a]-[1,4]benzodiazepines by heating a 2-[3-(phthalimidomethyl)-5-substituted-4H-1,2,4-triazol-4-yl]benzophenone with hydrazine hydrate in ethanol. However, there is no disclosure therein of using that process to cyclize products having a 5-halo-substituent on the triazole ring of the triazolylbenzophenone intermediate.

U.S. patent application Ser. No. 391,647, filed Aug. 27, 1973, now U.S. Pat. No. 3,891,666, describes a process for reacting a mixture of 5-chloro-2-(3-bromo-5-methyl-4H-1,2,4-triazol-4-yl)benzophenone with hydrazine or its mineral acid salt and a base in a lower alkanol, e.g., ethanol at 70°–120° C. to give 8-chloro-1-methyl-6-phenyl-4H-s-triazolo[4,3-a][1,3,4]benzotriazepine, indicating that hydrazine reacts with halogen on the triazole ring of triazolylbenzophenone compounds.

Similarly, U.S. Pat. No. 3,880,878 describes the reaction of a 5-(substituted aminomethyl)-3-halo substituted triazole moiety on a triazolylbenzophenone with hydrazine or a hydrazine salt and a base at 70° to 120° C. to close the benzotriazepine ring and thus to obtain a 1-(substituted aminomethyl)-6-phenyl-4H-s-triazolo[4,3-a][1,3,4]benzotriazepine, indicating again the hydrazine reacts with triazole-ring-bound halogen in triazolylbenzophenone reactants to form triazolobenzotriazepine compounds.

From the above histroy of this process chemistry one would expect therefore that a process route involving the use of hydrazine and a halo-substituted triazolylbenzophenone should not be used to prepare halogen-substituted triazolobenzodiazepines because in doing so would be expected that the triazolo-ring-bound-halogen would react with the hydrazine, thus defeating the object or purpose of the reaction.

OBJECTS OF THE INVENTION

It is an object of this invention to provide an improved process for preparing halogen-substituted triazolobenzodiazepines from benzophenone starting materials.

It is a more specific object of this invention to provide 1-halo-6-phenyl-4H-s-triazolo[4,3-a][1,4]benzodiazepines from 3-phthalimidomethyltriazolobenzophenones and hydrazine or a primary amine.

It is another object of this invention to improve processes for preparing 1-halo-6-phenyl-4H-s-triazolo[4,3-a]-[1,4]benzodiazepines by providing process conditions for the preferential displacement and benzodiazepine ring closure by hydrazine or a primary amine of the triazol-ring-bound-reactive-group which will permit the retention of triazolering-bound-halogen in a triazolylbenzophenone reactant.

Other objects, advantages and aspects of the invention will be apparent from reading the remaining specification and claims which follow.

SUMMARY OF THE INVENTION

Briefly, according to this invention, it has been discovered that 1-halo-6-phenyl-4H-s-triazolo[4,3-a][1,4]benzodiazepines can be prepared by reacting a 2-[3-(phthalimidomethyl)-4H-1,2,4-triazol-4-yl]benzophenone with an N-halosuccinimide to form the 2-[5-halo-3-(phthalimidomethyl)-4H-1,2,4-triazol-4-yl]benzophenone, and then reacting the 2-[5-halo-3-(phthalimidomethyl)-4H-1,2,4-triazol-4-yl]benzophenone with from about 1 molar equivalent to less than 2 molar equivalents of hydrazine or with two or more molar equivalents of a primary amine in an inert organic liquid at 25° to 100° C. until the 1-halo-6-phenyl-4H-s-triazolo[4,3-a][1,4]benzodiazepine is produced.

It has been surprisingly found that contrary to what would be expected from prior experience, this combination of reactants and process conditions preferentially effects the displacement of the phthalimido moiety over the halogen moiety on the triazole ring as well as the desired benzodiazepine ring closure reaction to obtain the desired useful 1-halo-6-phenyl-4H-s-triazolo[4,3-a][1,4]benzodiazepine. This process, then, significantly reduces the number of steps previously thought necessary to prepare a 1-halo-6-phenyl-4-H-s-triazolo[4,3-a][1,4]benzodiazepine type compound.

DETAILED DESCRIPTION OF THE INVENTION

More specifically, this invention provides a process for preparing a 1-halo-6-phenyl-4H-s-triazolo]4,3-a][1,4]benzodiazepine compound of the formula

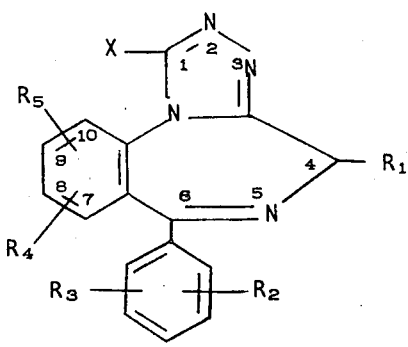

(I)

wherein
X is chloro or bromo,
$R_1$ is hydrogen or $C_1$ to $C_3$-alkyl, each of $R_2$, $R_3$, $R_4$, and $R_5$ is hydrogen, $C_1$ to $C_3$-alkyl, fluorine, chlorine, bromine, nitro, cyano or trifluoromethyl, with the proviso that not more than one of $R_2$ and $R_3$ on the 6-phenyl moiety and not more than one of $R_4$ and $R_5$ on the benzo moiety is $C_1$ to $C_3$-alkyl, nitro, cyano or trifluoromethyl,
which comprises A. reacting a benzophenone compound of the formula

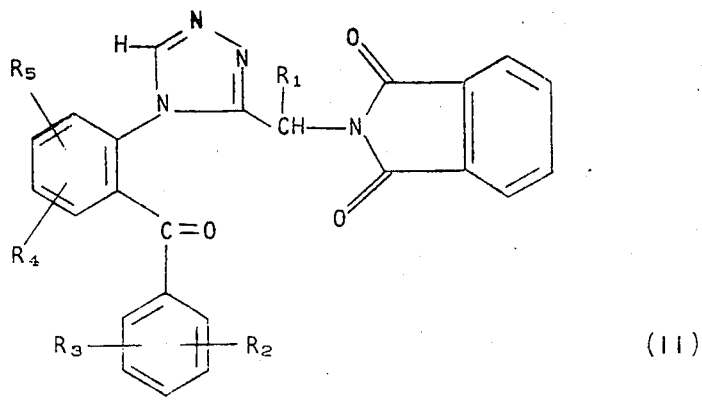

(II)

where $R_1$, $R_2$, $R_3$, $R_4$ and $R_5$ are as defined above, with an N-halo-carboxylic acylamide wherein the halo is bromo or chloro, in an inert, organic solvent medium at a temperature of from about 50° C. to the reflux temperature of the solvent system employed, but at a temperature below the decomposition point of the reactants, until there is formed a compound of the formula

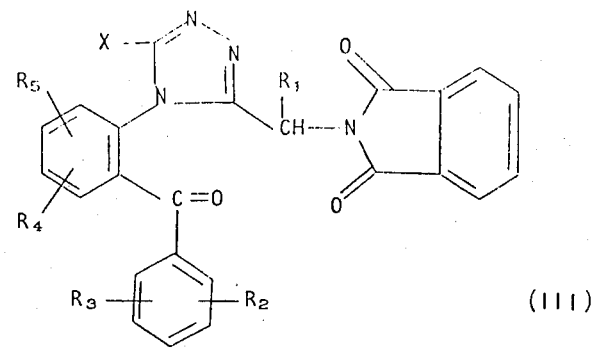

(III)

where X is bromo or chloro, and $R_1$, $R_2$, $R_3$, $R_4$, and $R_5$ are as defined above, and B. reacting a compound of formula (III) above with from about 1 molar equivalent but less than about two molar equivalents of hydrazine or with two or more molar equivalents of a primary amine in an inert, organic liquid solvent containing medium at a temperature of from about 25° C. to about 100° C. until an optimum amount of the 1-halo-6-phenyltriazolo[4,3-a][1,4]benzodiazepine compound of formula (I) above is formed. In this reaction it is advantageous to use the lowest temperatures and shortest reaction times possible that are still consistent with a reasonable reaction rate.

The 2-[3-(phthalimidomethyl)-4H-1,2,4-triazol-4-yl]-benzophenones which can be used to prepare the corresponding 5-halo compounds as described above are now known, having been described, e.g., in U.S. Pat. No. 3,842,090 and South African Pat. No. 74/0466 which are incorporated herein by reference thereto for that description. Representative examples of such starting materials include:

2-[3-(phthalimidomethyl)4H-1,2,4-triazol-4-yl]benzophenone,
5-bromo-2-[3-(phthalimidomethyl)-4H-1,2,4-triazol-4-yl]-5-benzophenone,
2',5-dichloro-2-[3-(phthalimidomethyl)-4H-1,2,4-triazol-4-yl]benzophenone,
5-nitro-2',6'-difluoro-2-[3-(phthalimidomethyl)-4H-1,2,4-triazol-4-yl]benzophenone,
5-trifluoromethyl-2'-bromo-2-[3-(phthalimidomethyl)-1,2,4-triazol-4-yl]benzophenone,
5-cyano-2'-nitro-2-[3-(phthalimidomethyl)-4H-1,2,4-triazol-4-yl]benzophenone,
5-ethyl-4'-(trifluoromethyl-2-[3-(phthalimidomethyl)-4H-1,2,4-triazol-4-yl)benzophenone,
2',5,6-trichloro-2-[3-(phthalimidomethyl)-4H-1,2,4-triazol-4-yl]benzophenone,
5-chloro-2-[3-(phthalimidomethyl)-4H-1,2,4-triazol-4-yl]benzophenone,
5-fluoro-2-[3-(phthalimidomethyl)-4H-1,2,4-triazol-4-yl]benzophenone,
2'-chloro-2-[3-(phthalimidomethyl)-4H-1,2,4-triazol-4-yl]benzophenone,
5-chloro-2'-fluoro-2-[3-(phthalimidomethyl)-4H-1,2,4-triazol-4-yl]benzophenone,
2'-chloro-5-nitro-2[3-(phthalimidomethyl)-4H-1,2,4-triazol-4-yl]benzophenone,
5-trifluoromethyl-2-[3-(phthalimidomethyl)-4H-1,2,4-triazol-4-yl]benzophenone,
5-nitro-2-[3-(phthalimidomethyl)-4H-1,2,4-triazol-4-yl]benzophenone, and the like.

The 2-[3-(phthalimidomethyl)-4H-1,2,4-triazol-4-yl]-benzophenone reactant is reacted with a halogenating agent, e.g., by heating it with an N-bromo or N-chlorosuccinimide or some other halogenating agent such as N-bromo or N-chloro-$C_1$ to $C_6$-alkanoylamide, e.g., N-bromo- or N-chloroacetamide, propionamide, caproamide, or other economical halogenating agent such as N-bromo or N-chlorophthalimide, or the like. For reasons of economy and availability, N-bromosuccinimide and N-chlorosuccinimide are preferred. The halogenation reaction can be carried out in an inert, organic, non-polar, liquid solvent, e.g., methylene chloride, chloroform, carbon tetrachloride, ethylene dichloride, benzene, toluene at a temperature of from about 46° C. to the reflux temperature of the solvent system employed. The heating is continued until analysis of samples of the reaction mixture indicate that the halogenation is essentially complete. Depending on the reactants, the temperature of the reaction medium and solvent system employed heating of the mixture at atmospheric pressure for from about 4 to about 18 hours is usually sufficient to essentially complete the halogenation.

The 2-[5-halo-3-(phthalimidomethyl)-4-H-1,2,4-triazol-4-yl]benzophenone intermediate can be isolated from the reaction mixture by usual procedures, if desired, or the reaction mixture can be used as such in the benzodiazepine ring closing reaction step (B) which follows. Since most of these intermediates will crystallize from the reaction mixture upon concentration of the reaction mixture and cooling, if necessary, it is preferred for easier handling to at least precipitate a crude crystalline form of the halogenated intermediate (III), before proceding. However, to insure a higher degree of purity the halogenated intermediate (III) can be recovered and purified by conventional procedures, e.g., extraction, crystallization, washing, column chromatography, and the like, if desired.

The 2-[5-halo-3-(phthalimidomethyl)-4H-1,2,4-triazol-4-yl]benzophenone intermediate (III) is mixed in an appropriate inert, organic liquid solvent medium with preferably not more than about 2 moles of hydrazine, hydrazine hydrate, a convenient mineral acid salt form of hydrazine, e.g., hydrazine hydrochloride, hydrazine sulfate, hydrazine phosphate, or the like or with 2 or more molar equivalents of a primary amine which is dispersible in the organic solvent medium. If a primary amine is used it is preferred for reasons of ease of solubility in the usual solvents that a $C_1$ to $C_6$-alkylamine, e.g., methylamine, ethylamine, butylamine, hexylamine be used. Methylamine, being a gas at atmospheric pressure would be bubbled into the reaction mixture or used as a commercially available solution in water. Other primary amines could be used but those exemplified above are the preferred ones.

Solvent systems for this step include $C_1$ to $C_6$-alkanols, cyclohexanol, ethylene glycol, monoglyme, diglyme, tetrahydrofuran, bis $C_2$ to $C_4$-alkyl ethers, dimethylsulfoxide, dimethylformamide and dimethylacetamide, as well as commercially available polar solvent mixtures having boiling point ranges sufficiently high to permit refluxing in the above indicated temperature ranges to assist in heat distribution and efficient mixture and solution of the reactants. Small incidental amounts of water, say, less than about 5 percent by volume of the reaction mixture, introduced with the reactants or solvent systems used are not substantially detrimental to the process.

The hydrazine or primary amine reactant can be added alone or in a suitable solvent dropwise, portionwise or all at once to a stirred solution of the 2-[5-halo-3-(phthalimidomethyl)-4H-1,2,4-triazol-4-yl]benzophenone in a solvent until up to about 2 molar equivalents of hydrazine or two or more molar equivalents of the primary amine are added, relative to the molar content of the benzophenone. Alternatively, the desired proportions of 2-[5-halo-3-(phthalimidomethyl)-4H-1,2,4-triazol-4-yl)benzophenone and hydrazine or primary amine reactant can be mixed initially in the cold with or in an appropriate solvent system and then warmed and stirred to effect reaction.

It is understood that if less than 1 molar equivalent of hydrazine or two molar equivalents of the primary amine are used the ring closure reaction will proceed but some of the expensive triazolo benzophenone starting material will not react. Similarly, as the amount of hydrazine exceeds the suggested upper limit the ring bound halogen will react, and to the extent making the process less efficient.

Prolonged reaction times or excessively high reaction temperatures in the presence of excess hydrazine or primary amine reactant will promote reaction thereof with the triazole-ring-bound halogen, thereby defeating the purpose of this process route. To minimize such side reactions it is preferred to use between about 1 and 1.5 molar proportions of hydrazine and a reaction temperature of between 25 and 80° C. for a period of time sufficient to complete the reaction, normally within 1 to 5 hours. With the less reactive primary amines two or more molar equivalents of the amine reagent can be used. However, when a primary amine is used the temperature of the reaction mixture should be kept as low as possible, consistant with a reasonable reaction rate, normally 25°–50° C. The reaction should be monitored to avoid prolonged exposure of the products of the reaction to the excess amine reagent. Normally, 1 to 24 hours will be required for this reaction depending on the primary amine reagent, the solvent and the temperature.

The ring closing reaction can generally be accomplished in from 1 to about 5 hours at 25° to about 100° C. using hydrazine or a reactive form thereof in a $C_1$ to $C_6$-alkanol with most combinations of reactants. If the reaction is conducted using a primary amine such as a $C_1$ to $C_6$-alkylamine, e.g. with methylamine, ethylamine, propylamine, butylamine, isobutylamine, hexylamine or the like, the reaction times and temperatures may vary somewhat. Using methylamine, the phthalimide group can be removed and benzodiazepine ring closure can be effected at 25°–50° C. during 1 to 18 hours in solvents such as methylene chlorides, tetrahydrofuran, or a $C_1$ to $C_6$-alkanol in mixtures thereof.

Upon completion of the reaction, the resulting reaction mixture can be worked up by conventional procedures to isolate therefrom the desired 1-halo-6-phenyl-4H-s-triazolo-[4,3-a][1,4]benzodiazepine. For example, if the reaction is carried out in ethanol with hydrazine the mixture can be cooled and filtered. The solid precipitate which consists of a biproduct can be washed with an appropriate solvent to recover therefrom any adhering product. The original and wash filtrate containing the product can be concentrated, mixed with water, and the resulting mixture extracted with a water immissible solvent such as chloroform or methylene chloride to take up the benzodiazepine product. The extract can be washed, dried and concentrated to promote crystallization of the benzodiazepine product. To effect further purification of the benzodiazepine can be re-dissolved and re-crystallized from an organic liquid solvent such as ethyl acetate, after treatment of the ethyl acetate solution of the product with a decolorizing charcoal, if desired. These 1-halo-6-phenyl-4H-s-triazolo[4,3-a][1,4]benzodiazepines are crystalline compounds which may decompose somewhat at their melting points.

The invention is further exemplified by the following detailed examples which are not intended to limit the scope of the invention.

EXAMPLE 1

A. 5-Chloro-2-[3-bromo-5-(phthalimidomethyl)-4H-1,2,4-triazol-4-yl]benzophenone

A mixture of 4.43 g. (0.01 mole) of 5-chloro-2-[3-(phthalimdomethyl)-4H-1,2,4-triazol-4-yl]benzophenone, 2.31 g. (0.013 mole) of N-bromosuccinimide, and 250 ml. of benzene is stirred and refluxed under a nitrogen atmosphere for 7 hours and then kept at ambient temperature for 18 hours to insure complete reaction. The reaction mixture is concentrated in vacuo and the residue is mixed with water and extracted with chloroform. The chloroform extract is washed with brine (saturated aqueous NaCl), dried over sodium sulfate and concentrated. The residue is crystallized from a methylene chloride/methanol mixture with decolorizing charcoal (Darco brand) to give a 3.00 g. crop of 5-chloro-2-[3-bromo-5-(phthalimidomethyl)-4H-1,2,4-triazol-4-yl]benzophenone, m.p. 201.5°–203.5° C. and another 1.05 g. crop of the same compound, m.p. 201.5°–202.5° C. A purified analytical sample of this compound had a melting point of 204°–205° C. and analyzed Anal. Calcd. for $C_{24}H_{14}BrClN_4O_3$: C, 55.25; H, 2.70; N, 10.74; C, 55.15; H, 2.59; N, 10.91.

B. 1-Bromo-8-chloro-6-phenyl-4H-s-triazolo[4,3-a][1,4]-benzodiazepine

A mixture of 1.04 g. (0.002 mole) 5-chloro-2-[3-bromo-5-(phthalimidomethyl)-4H-1,2,4-triazol-4-yl]benzophenone, prepared as described above, and 10 ml. of absolute ethanol is stirred and treated with 0.15 ml. (0.003 mole) of hydrazine hydrate and warmed, under nitrogen, to 77° C. during 45 minutes. The reaction mixture then is kept at 55°–77° C. for about 1 hour and 35 minutes to insure complete reaction, cooled and filtered. The solid is washed with ethanol and methylene chloride and then combined filtrate is concentrated. The residue is mixed with water and extracted with chloroform. The chloroform extract is washed with brine, dried over sodium sulfate and concentrated. The residue is crystallized twice from ethylacetate containing a decolorizing charcoal (Darco) to give a 0.324 g. crop of 1-bromo-8-chloro-6-phenyl-4H-s-triazolo[4,3-a][1,4]benzodiazepine, m.p. 205.5°–206° C. with decomposition, and another 0.070 g. crop of the same compound, melting at 204.5°–205° C. for a 52.8 percent yield.

EXAMPLE 2

1-Chloro-8-bromo-6-phenyl-4H-s-triazolo[4,3-a]-[1,4benzodiazepine

A. 5-Bromo-2-[3-chloro-5-(phthalimidomethyl)-4H-1,2,4-triazol-4-yl]benzophenone

5-Bromo-2-[3-(phthalimidomethyl)-4H-1,2,4-triazol-4-yl]-benzophenone (0.01 mole) and N-chlorosuccinimide (0.013 mole) in benzene is stirred and refluxed under a nitrogen atmosphere for 7 hours to give 5-bromo-2-[3-chloro-5-(phthalimidomethyl)-4H-1,2,4-triazol-4-yl]benzophenone.

B. 1-Chloro-8-bromo-6-phenyl-4H-s-triazolo[4,3-a][1,4-benzodiazepine

The product from A (0.01 mole) with 40% aqueous methylamine (7.8 ml., 0.1 mole) in ethanol (30 ml.) and methylene chloride (30 ml.) were allowed to react for 24 hours at 25° C., concentrated and then chromatographed on silica gel (250 gm.) with 2% methanol - 98% chloroform to give 1-chloro-8-bromo-6-phenyl-4H-s-triazolo[4,3-a][1,4]benzodiazepine.

EXAMPLE 3

1-Bromo-8-nitro-6-phenyl-4-H-s-triazolo[4,3-a]-[1,4]benzodiazepine

Following the procedure of Example 2, 5-nitro-2-[3-phthalimidomethyl-4H-1,2,4-triazol-4-yl]benzophenone is reacted with N-bromosuccinimide to form 5-nitro-2-[3-bromo-5-phthalimidomethyl-4H-1,2,4-triazol-4-yl]benzophenone.

The 5-nitro-2-[3-bromo-5-phthalimidomethyl-4H-1,2,4-triazol-4H-1,2,4-triazol-4-yl]benzophenone is reacted with methylamine in ethanol to form the 1-bromo-8-nitro-6-phenyl-4H-s-triazolo[4,3-a][1,4]benzodiazepine.

EXAMPLE 4
1-Bromo-8-chloro-6-2(2-chloro-phenyl)-4H-s-triazolo[4,3-a][1,4]benzodiazepine Following the procedure of Example 1, 2',5-dichloro-2-[3-phthalimidomethyl-4H-1,2,4-triazol-4-yl]benzophenone is reacted with N-bromosuccinimide to form the 2',5-dichloro-2-[3-bromo-5-phthalimidomethyl-4H-1,2,4-triazol-4-yl]benzophenone.

The 2',5-dichloro-2-[3-bromo-5-phthalimimidomethyl-4H-1,2,4-triazol-4-yl]benzophenone is reacted with hydrazine by the general procedure of Example 1 to form 1-bromo-8-chloro-6-(2-chloro-phenyl)-4H-s-triazolo[4,3-a][1,4]benzodiazepine.

EXAMPLE 5
1-Chloro-8-nitro-6-(2,6-difluoro)-phenyl-4H-s-triazolo[4,3-a][1,4]benzodiazepine Following the procedure of Example 1, 5-nitro-2-[3-phthalimidomethyl-4H-1,2,4-triazol-4-yl]-2',6'-difluorobenzophenone is reacted with N-chloroacetamide to form 5-nitro-2-[3-chloro-5-phthalimidomethyl-4H-1,2,4-triazol-4-yl]-2',6'-difluorobenzophenone.

The 5-nitro-2-[3-chloro-5-phthalimidomethyl-4H-1,2,4-triazol-4-yl]-2',6'-difluorobenzophenone is reacted with hydrazine by the procedure of Example 1 to form the titled compound.

EXAMPLE 6
1-Bromo-8-trifluoromethyl-6-(2-bromo-phenyl)-4H-s-triazolo[4,3-a][1,4]benzodiazepine Following the procedure of Example 1, 5-trifluoromethyl-2-[3-phthalimidomethyl-4H-1,2,4-triazol-4-yl]-2'-bromobenzophenone is reacted with N-bromosuccinimide to form 5-trifluoromethyl-2-[3-bromo-5-phthalimidomethyl-4H-1,2,4-triazol-4-yl]-2'-bromobenzophenone.

The 5-trifluoromethyl-2-[3-bromo-5-phthalimidomethyl-4H-1,2,4-triazol-4H-yl]-2'-bromobenzophenone is reacted with hydrazine by the procedure of Example 1 to form the titled compound.

EXAMPLE 7
1-Chloro-8-fluoro-6-phenyl-4H-s-triazolo[4,3-a][1,4]benzodiazepine

Following the procedure of Example 2, 5-fluoro-2-[3-phthalimidomethyl-4H-1,2,4-triazol-4-yl]benzophenone is reacted with N-chlorosuccinimide to form 5-fluoro-2-[3-chloro-5-phthalimidomethyl-4H-1,2,4-triazol-4-yl]benzophenone.

The 5-fluoro-2-(3-chloro-5-phthalimidomethyl-4H-1,2,4-triazol-4-yl)benzophenone is reacted with ethylamine to form the titled product.

EXAMPLE 8
1-Bromo-6-phenyl-4H-s-triazolo[4,3-a][1,4]benzodiazepine

Following the procedure of Example 1, 2-(3-phthalimidomethyl-4H-1,2,4-triazol-4-yl)benzophenone is reacted with N-bromosuccinimide to form 2-(3-bromo-5-phthalimidomethyl-4H-1,2,4-triazol-4-yl)benzophenone.

The 2-(3-bromo-5-phthalimidomethyl)-4H-1,2,4-triazol-4-yl)benzophenone is reacted with hydrazine to form the title product.

EXAMPLE 9
1-Chloro-6-(2-chlorophenyl)-4H-s-triazolo[4,3-a]-[1,4]benzodiazepine Following the procedure of Example 2, 2-(3-phthalimidomethyl-4H-1,2,4-triazol-4-yl)-2'-chlorobenzophenone is reacted with N-chlorophthalimide to form 2-(3-chloro-5-phthalimidomethyl-4H-1,2,4-triazol-4-yl)-2'-chlorobenzophenone.

The 2-(3-chloro-5-phthalimidomethyl-4H-1,2,4-triazol-4-yl)-2'-chlorobenzophenone is reacted with propylamine to form the title compound.

EXAMPLE 10
1-Bromo-8-chloro-6-(2-fluorophenyl)-4H-s-triazolo[4,3-a][1,4]benzodiazepine Following the procedure of Example 1, 5-chloro-2-(3-phthalimidomethyl-4H-1,2,4-triazol-4-yl)-2'-fluorobenzophenone is reacted with N-bromosuccinimide to form 5-chloro-2-(3-bromo-5-phthalimidomethyl-4H-1,2,4-triazol-4-yl)-2'-fluorobenzophenone.

The 5-chloro-2-(3-bromo-5-phthalimidomethyl-4H-1,2,4-triazol-4-yl)-2'-fluorobenzophenone is reacted with hydrazine to form the titled compound.

EXAMPLE 11
1-Bromo-8-nitro-6-(2-chlorophenyl)-4H-s-triazolo[4,3-a][1,4]benzodiazepine Following the procedure of Example 1, 5-nitro-2-(3-phthalimidomethyl-4H-1,2,4-triazol-4-yl)-2'-chlorobenzophenone is reacted with N-bromophthalimide to form 5-nitro-2-(3-bromo-5-phthalimidomethyl-4H-1,2,4-triazol-4yl)-2'-chlorobenzophenone.

The 5-nitro-2-(3-bromo-5-phthalimidomethyl-4H-1,2,4-triazol-4-yl)-2'-chlorobenzophenone is reacted with hydrazine to form the titled compound.

EXAMPLE 12
1-Bromo-8-trifluoromethyl-6-phenyl-4H-s-triazolo[4,3-a][1,4]benzodiazepine Following the procedure of Example 1, 5-trifluoromethyl-2-(3-phthalimidomethyl-4H-1,2,4-triazol-4-yl)benzophenone is reacted with N-bromosuccinimide to form 5-trifluoromethyl-2-(3-bromo-5-phthalimodomethyl-4H-1,2,4-triazol-4-yl)benzophenone.

The 5-trifluoromethyl-2-(3-bromo-5-phthalimidomethyl-4H-1,2,4-triazol-4-yl)benzophenone is reacted with hydrazine to form the titled product.

EXAMPLE 13
1,8-Dichloro-6-phenyl-4H-s-triazolo[4,3-a][1,4]-benzodiazepine

Following the procedure of Example 1, 5-chloro-2-(3-phthalimidomethyl-4H-1,2,4-triazol-4-yl)benzophenone is reacted with N-chlorohexanoamide to form 5-chloro-2-(3-chloro-5-phthalimidomethyl-4H-1,2,4-triazol-4-yl)benzophenone.

The 5-chloro-2-(3-chloro-5-phthalimidomethyl-4H-1,2,4-triazol-4-yl)benzophenone is reacted with hydrazine to form the titled compound.

EXAMPLE 14
1,8-Dichloro-4-methyl-6-phenyl-4H-s-triazolo[4,3a][1,4]benzodiazepine Following the procedure of Example 1, 5-chloro-2-[3-(1-phthalimidoethyl)-4H-1,2,4-triazol-4yl]benzopheone is reacted with N-chlorosuccinimide to form 5-chloro-2-[3-chloro-5-(1-phthalimidoethyl)-4H-1,2,4-triazol-4-yl]benzophenone.

The 5-chloro-2-[3-chloro-5-(1-phthalimidoethyl)-4H-1,2,4-triazol-4-yl]benzophenone is reacted with hydrazine to form the titled product.

I claim:

1. Process for preparing a 1-halo-6-phenyl-4H-s-triazolo-[4,3-a][1,4]benzodiazepine compound of the formula

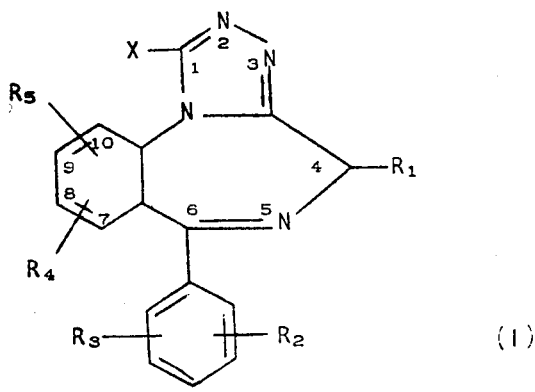

(I)

wherein
X is chloro or bromo,
$R_1$ is hydrogen, or $C_1$ to $C_3$-alkyl,
each of $R_2$, $R_3$, $R_4$, and $R_5$ is selected from the group consisting of hydrogen, $C_1$ to $C_3$-alkyl, fluorine, chlorine, bromine, nitro, cyano and trifluoromethyl, with the proviso that not more than one of $R_2$ and $R_3$ on the 6-phenyl moiety and not more than one of $R_4$ and $R_5$ on the benzo moiety is $C_1$ to $C_3$-alkyl, nitro, cyano or trifluoromethyl,
which comprises (A) reacting a benzophenone compound of the formula II

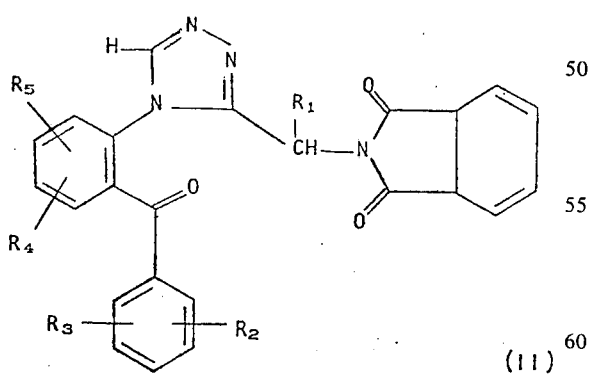

(II)

wherein $R_1$, $R_2$, $R_3$, $R_4$ and $R_5$ are as defined above with an N-haloacylimide wherein the halo is bromo or chloro in an organic liquid solvent medium at a temperature of from about 46° C. to the reflux temperature of the solvent system employed until there is formed a compound of the formula

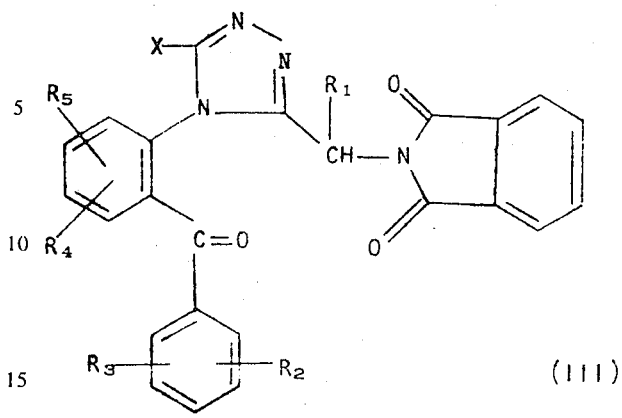

(III)

where X is bromo or chloro, and
$R_1$, $R_2$, $R_3$, $R_4$ and $R_5$ are as defined above, and then
B. reacting a compound of formula (III) above with from about 1 to about 2 molar equivalents of hydrazine or with at least about 2 molar equivalents of a primary amine in an inert organic liquid solvent medium at a temperature of from about 25° to 100° C. until the benzodiazepine compound of formula (I) is prepared.

2. Process of claim 1 wherein in step (A) N-bromosuccinimide is reacted with a benzophenone compound of formula (II) wherein $R_1$ is hydrogen, $R_2$ and $R_3$ are each hydrogen, $R_4$ is 5-chloro, and $R_5$ is hydrogen, and in step (B) the product of step (A) is reacted with hydrazine to form 1-bromo-8-chloro-6-phenyl-4-H-s-triazolo[4,3-a][1,4]benzodiazepine.

3. In a process for preparing a 1-halo-6-phenyl-4H-s-triazolo-[4,3a][1,4]benzodiazepine compound of the formula

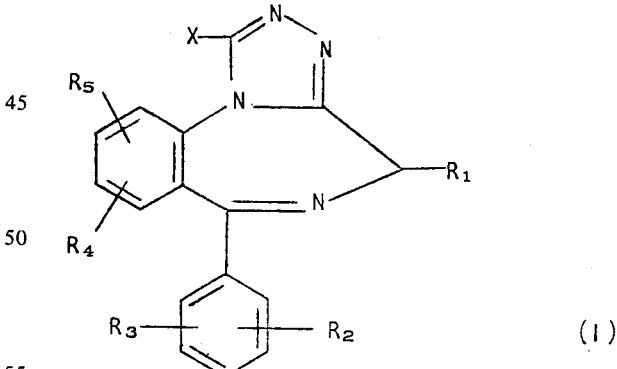

(I)

wherein X is bromo or chloro,
$R_1$ is hydrogen or $C_1$ to $C_3$-alkyl, each of $R_2$, $R_3$, $R_4$ and $R_5$ is selected from the group consisting of hydrogen, $C_1$ to $C_3$-alkyl, fluorine, chlorine, bromine, nitro, cyano and trifluoromethyl, with the proviso that not more than one of $R_2$ and $R_3$ on the 6-phenyl moiety and not more than one of $R_4$ and $R_5$ on the benzo moiety is $C_1$ to $C_3$-alkyl, nitro, cyano or trifluoromethyl, the improvement which comprises reacting a benzophenone compound of the formula

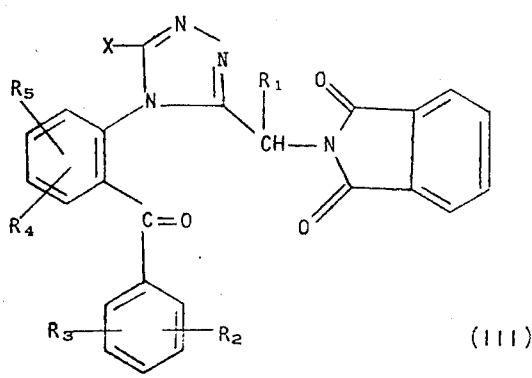

(III)

wherein X, $R_1$, $R_2$, $R_3$, $R_4$ and $R_5$ are as defined above, with from about 1 to about 2 molar equivalents of hydrazine or with about 2 or more molar equivalents a $C_1$ to $C_6$-alkyl-primary amine in an organic liquid solvent medium at a temperature of from about 25° to about 100° C. until the benzodiazepine compound of formula (I) is prepared.

4. Process of claim 3 wherein a benzophenone compound of formula (III) wherein X is bromo, $R_1$ is hydrogen, $R_2$, $R_3$ and $R_5$ are hydrogen, $R_4$ is 5-chloro is reacted with hydrazine to prepare 1-bromo-8-chloro-6-phenyl-4H-s-triazolo[4,3-a][1,4]-benzodiazepine.

* * * * *